United States Patent

Prouvost

[11] Patent Number: 5,962,780
[45] Date of Patent: Oct. 5, 1999

[54] MEASURING DEVICE

[75] Inventor: Hubert Prouvost, Pau, France

[73] Assignee: Elf Exploration Production, France

[21] Appl. No.: 09/037,914

[22] Filed: Mar. 9, 1998

[51] Int. Cl.[6] .................................................. G01F 15/02
[52] U.S. Cl. ........................................................ 73/198
[58] Field of Search .............................. 73/195, 198, 200,
73/64.56, 19.1; 324/693, 694, 698

[56] References Cited

U.S. PATENT DOCUMENTS

| | | | |
|---|---|---|---|
| 3,233,448 | 2/1966 | Brown | 73/53 |
| 4,168,624 | 9/1979 | Pichon | 73/195 |
| 4,236,406 | 12/1980 | Reed et al. | 73/61.1 |
| 4,429,581 | 2/1984 | Furmaga | 73/195 |
| 5,001,434 | 3/1991 | Marrelli et al. | 324/640 |
| 5,033,288 | 7/1991 | Castel | 73/61.1 |
| 5,233,861 | 8/1993 | Gore et al. | 73/1.16 |
| 5,239,862 | 8/1993 | Atkinson | 73/64.44 |
| 5,363,696 | 11/1994 | Cardellini et al. | 73/61.44 |
| 5,608,170 | 3/1997 | Atkinson et al. | 73/861.04 |

*Primary Examiner*—Robert Raevis
*Attorney, Agent, or Firm*—Bacon & Thomas, PLLC

[57] ABSTRACT

Measuring device comprising a flow meter (26) provided with an inlet and an outlet which are each intended to be connected to a conduit in which a polyphase outflow to be measured flows, originating, for example, from an oil well, and a first valve (28) arranged below the flow meter (26), the flow meter being mounted generally vertically. According to the invention, the device furthermore comprises a branch passage (34), provided with a second valve (36), opening above the flow meter, so that it can be filled selectively with liquid using this branch passage (34).

4 Claims, 2 Drawing Sheets

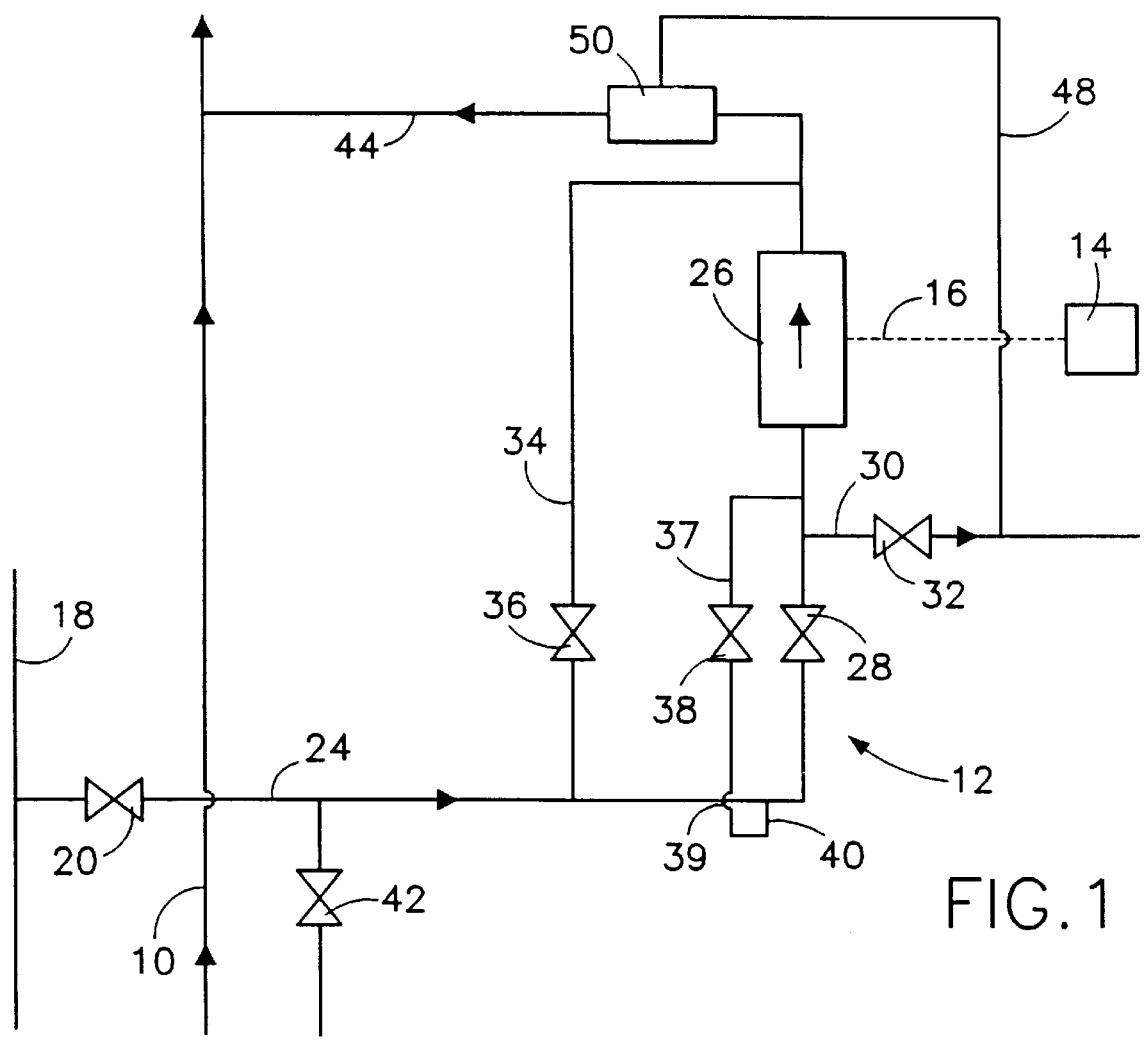
FIG. 1
FIG. 2
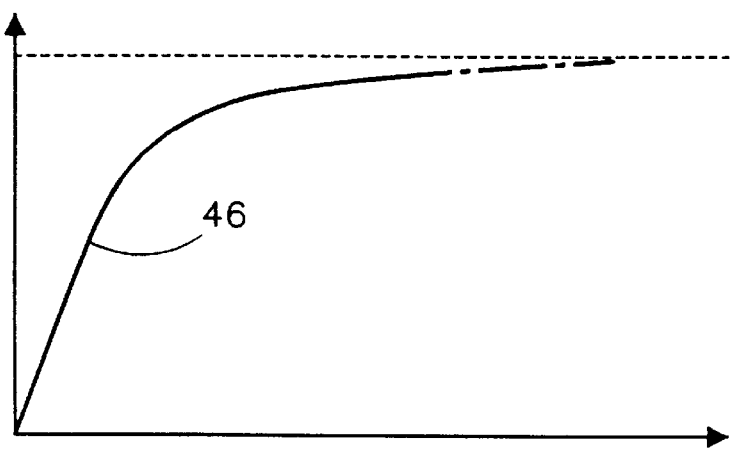

MEASURING DEVICE

BACKGROUND OF THE INVENTION

1. Field of the Invention

The present invention relates to a measuring device and, more particularly, to a device of this type intended to provide measurements relating to petroleum outflow originating from a well.

2. Description of Related Art

When an oil well is set in production, it is necessary to characterize the outflows originating from the well in order to manage the production better.

This characterization is generally done by complex analyses which demand very specific sampling conditions. For example, it may be necessary to take a sample of the oil phase and/or of the/a gas phase at well-defined pressure and temperature conditions.

Furthermore, during the well production period, it is necessary to monitor the change in the characteristics of the outflow, as well as the quantities produced, in order to manage the reservoir better. This monitoring is generally done by analyses and flow-rate measurements which involve measuring the various physical characteristics of the outflow, such as the flow rates of each of the phases, their density and the salinity of the water.

However, since the nature of the outflow changes during the reservoir production period, it is necessary to periodically recalibrate the device which measures the characteristics of the outflow, and preferably takes samples of its constituents.

For example, when the flow meter is of the type in which some of the measurements taken are based on the conductivity of the water present in the outflow, and since this conductivity can change with time, it is essential to know it. It has hitherto been known generally by virtue of periodic analyses which require samples to be taken.

SUMMARY OF THE INVENTION

The object of the present invention is therefore a measuring device which is designed to provide measurements of various physical characteristics of a polyphase fluid, which can be recalibrated easily without requiring analyses performed in a laboratory, nor even on-site intervention, and which makes it possible to take samples of each of the phases forming the outflow.

In order to achieve this object, the invention proposes a measuring device comprising a flow meter (26) provided with an inlet and an outlet which are each intended to be connected to a conduit in which a polyphase fluid to be measured flows, and a first valve (28) arranged below the flow meter (26), the flow meter being mounted generally vertically, characterized in that it furthermore comprises a bypass passage (34), provided with a second valve (36), opening above the flow meter, so that it can be filled selectively with liquid using this bypass passage (34).

The invention makes it possible to monitor the conductivity by measuring it in the flow meter itself, without taking a sample, by isolating a water sample of the outflow in the measuring device for the purpose of analysis. This possibility is even more beneficial since, with some production mechanisms, for example those employing offshore wells, it may be impossible to take a sample without very expensive equipment.

Other characteristics and advantages of the present invention will emerge on reading the following description which is given, by way of explanation but without implying any limitation, with reference to the appended drawings.

BRIEF DESCRIPTION OF THE FIGURES OF DRAWINGS

FIG. 1 is a schematic view of a measuring device according to a first embodiment of the invention;

FIG. 2 represents the change in the conductivity as a function of time during the measurements taken in the device of FIG. 1.

DETAILED DESCRIPTION OF THE PREFERRED EMBODIMENT

Figure 3:
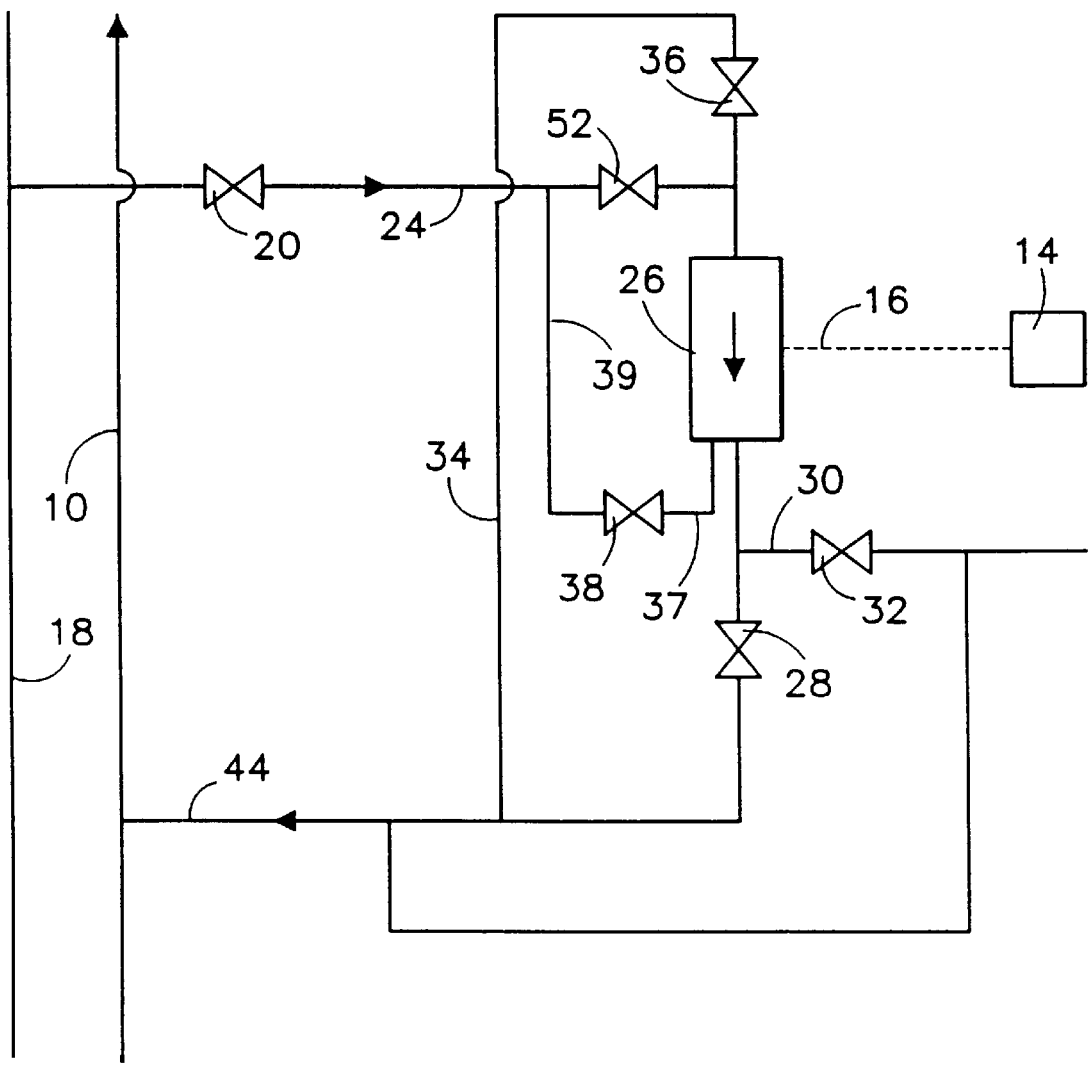
FIG. 3 is a schematic view of a measuring device according to a second embodiment of the invention.

FIG. 1 represents tubing 10 extending between an oil well and an outlet (these are not shown) and forming an effluent channel for a polyphase petroleum outflow originating from a well-bottom reservoir. The petroleum outflow is typically formed by a mixture of oil, water and gas in proportions which vary while the well is producing, the composition of each phase also varying.

A measuring device, represented generally at 12, is mounted in communication with the tubing 10, for example on the sea bed in the case of an offshore well, and a test manifold 18, of conventional design, which allows one or more wells to be placed in communication with the measuring device 12 by means of a valve 20 and a conduit 24. The measuring device makes it possible to provide measurements concerning the outflow to a remote station 14 using a transmission channel 16.

The measuring device 12 comprises a polyphase flow meter 26, of conventional design, mounted vertically in order to receive an ascending flow. This type of flow meter generally includes systems intended to measure the flow speed and the proportion of each phase forming the outflow. To do this, it uses parameters such as the conductivity, permittivity and gamma-ray absorption. The conduit 24 is intended to be connected selectively to the inlet of the polyphase flow meter 26 by a valve 28 controlled from the station 14. A conduit 30, opening between the valve 28 and the flow meter 26, and provided with a valve 32 also controlled from the station 14, forms an outlet making it possible to take outflow samples or to purge the lower part of the flow meter, as will be described in more detail below. A first bypass passage 34, provided with a valve 36, is arranged in parallel with the flow meter 26.

A second bypass passage 37, provided with a valve 38, opens directly below the flow meter 26. The diameter of the pipeline of the passage 37 is reduced at the level of the opening, so as to promote the settling of the liquid in the branch containing the flow meter 26, while limiting the quantity of the fluid passing through this branch. The production of the well is sent towards the bypass passage 34, so as to fill the branch containing the flow meter and provide the fluid with the pressure head needed for the bypass passage 37 to function properly. A conduit 39, which connects the valve 38 to the conduit 24, includes a segment 40 which descends below the level of the conduit 24 forming a non-return section. The conduit 24 is also provided with a purge valve 42. The valves 36 and 42 are controlled from the station 14. A conduit 44 connects the outlet of the polyphase flow meter 26 to the tubing 10.

The measuring device according to the invention makes it possible to take three types of measurement, namely flow-rate measurements, measurements used to calibrate the flow meter, and measurements of certain properties of each of the three phases. Since some of the measurements taken in the polyphase flow meter are based on the knowledge of physical parameters which are characteristic of each phase, for example the conductivity of the water present in the outflow, and since these characteristics can change while the well is producing, it is essential that the values of the parameters used to calibrate the flow meter be updated periodically.

Reciprocally, the measuring device makes it possible to measure the value of the physical parameters of a given phase, on condition that these parameters are not required for taking the measurement.

In order to take measurements of this type, the valves 28 and 38 are closed and the valve 36 is opened, which directs outflow in line with the polyphase flow meter 26 and discharges it through the conduit 44. In view of the respective density of the phases which are present, and of the arrangement of the conduits, the conduit portion delimited by the valve 28 (closed) and the junction between the bypass passage 34 and the top of the flow meter will fill with outflow, predominantly liquid. Since this liquid present in the flow meter is stationary, it separates into its three constituent phases, water and oil remaining inside the flow meter and the gas escaping through the conduit 44. In the conduit portion delimited by the valve 28 (closed) and the junction between the bypass passage 34 and the top of the flow meter, the water has a tendency, because of its density, to displace the oil and the gas which are present and to fill the inside of the flow meter 26. It is thus possible to take measurements of the physical parameters of just the water phase, for example the conductivity, either for the purpose of calibrating the equipment or for the purpose of ascertaining the characteristics of the water, as stated further above.

However, it may take a long time for the flow meter 26 to become filled exclusively with water. In order to shorten this measuring time, it is possible to prepare a graph of the change in the measured conductivity as a function of time while the flow meter 26 is filling with water, as represented in FIG. 2. On the basis of analysing a number of these graphs, the final value of the conductivity can be predicted by studying the initial part 46 of the curve, as represented by the broken line.

Once the measurements of the physical parameters of the water present in the flow meter are completed, and if it is desired to take measurements of the oil phase, the water is purged through the valve 32, so that the contents of the flow meter become concentrated in oil. The desired measurement of the oil can then be taken by using the graph whose structure is explained above and in FIG. 2. The operation of purging the water may need to be repeated, especially if the outflow fed into the flow meter contains a large proportion of water and the volume contained between the bottom of the measuring cell of the flow meter and the purge 32 is small. When the measurements of the characteristics of the oil have been taken, if it is desired to take measurements of the characteristics of the gas contained in the outflow, it is necessary to stop any circulation in the bypass passage 34 while keeping the valve 28 closed and draining the liquid. Care will need to be taken that the arrangement of the outlet conduit 44 is such that no liquid can flow back the wrong way, from the tubing 10 to the flow meter 26, for example by connecting the conduit 44 to the tubing 10 using an arrangement of the "goose neck" type or by installing a non-return valve on the conduit 44. Once these measurements of the characteristics of each phase have been completed, and the calibration parameters have been updated in the computer of the polyphase flow meter 26, the bypass passages 34 and 37 are closed, the valve 28 is opened and the flow-rate measurements can resume with updated calibration parameters. As an alternative, water, gas or oil present in the separated phase state in the flow meter 26 can be sampled via the conduit 30 by opening the valve 32. If a purge to the atmosphere is not desired, the outlet of the valve 32 will be directed through a conduit 48 to a head-loss device 50 mounted on the conduit 44, for example a partially closed valve. The head-loss device 50 may also consist of the low-pressure tap of a pressure reducer.

The measuring device according to the invention also includes the second branch passage 37 which, when the production from the well flows through the bypass passage 34 allows the enrichment of the liquid fraction of the outflow passing through the flow meter 26. The density of the fluid contained in the bypass passage 34 is less than that of the fluid contained in the branch containing the flow meter 26. This results in an internal circulation of fluid, from top to bottom of the flow meter, which then rejoins the liquid flowing in the bypass passage 34. It will be noted that this bypass passage 37 is mainly useful for outflows containing little liquid and a large amount of gas, because a small proportion of liquid makes it difficult to measure the characteristics of this liquid, irrespective of the measurement principle employed by the flow meter.

FIG. 3 represents a measuring device according to a second embodiment, in which the polyphase flow meter 26 is designed to receive a descending flow, and therefore in which the conduits 24 and 44 are reversed. This device differs from the one represented in FIG. 1 in that the first bypass passage 34 feeds outflow vertically above the flow meter, to its inlet, whereas in the first embodiment, this passage fed the fluid horizontally above the flow meter, to its outlet. In addition, the second bypass passage 37 no longer includes a segment 40, since the conduit 39 naturally descends. A valve 52 is mounted between the conduit 39 and the flow meter 26. In order to make it possible to supply the bypass passage 37, the valve 52 is constricted in order to create the required head difference. When it is not open to the atmosphere, the purge valve 32 is connected downstream of the valve 28. The head-loss device 50 used in the embodiment in FIG. 1 is no longer necessary in this embodiment. Under certain conditions, constriction of the valve 36 may be employed to produce the head loss needed to remove the liquid contents of the flow meter through the purge 32 into the conduit 44.

I claim:

1. A measuring device comprising a generally vertically mounted flow meter having an inlet and an outlet which are adapted to be connected to a conduit in which a polyphase fluid to be measured flows, a first valve arranged below the flow meter, a passage which bypasses the flow meter opening above the flow meter and having a second valve so that the flow meter can be filled selectively with liquid using this bypass passage and an outlet between the first valve and flow meter having a third valve to allow withdrawal of liquid from the flow meter.

2. The measuring device according to claim 1, wherein the flow meter is mounted so as to receive an ascending flow.

3. The measuring device according to claim 1, wherein the flow meter is mounted so as to receive a descending flow.

4. The measuring device according to claim 1, further comprising a second passage provided with a fourth valve arranged in parallel with the first valve.

* * * * *